United States Patent

Ramamurthy et al.

[11] Patent Number: 6,015,384
[45] Date of Patent: Jan. 18, 2000

[54] ULTRASONIC SYSTEM AND METHOD FOR TISSUE VIABILITY IMAGING

[75] Inventors: Bhaskar S. Ramamurthy, San Jose; Joan C. Main, Mountain View, both of Calif.

[73] Assignee: Acuson Corporation, Mountain View, Calif.

[21] Appl. No.: 09/144,843

[22] Filed: Aug. 31, 1998

[51] Int. Cl.[7] .................................. A61B 8/00; A61B 8/06
[52] U.S. Cl. .......................... 600/440; 600/441; 600/455
[58] Field of Search ................................... 600/440–441, 600/454–456

[56] References Cited

U.S. PATENT DOCUMENTS

| | | |
|---|---|---|
| 4,550,607 | 11/1985 | Maslak et al. . |
| 4,824,660 | 4/1989 | Angello et al. . |
| 5,206,222 | 4/1993 | Forman et al. . |
| 5,224,175 | 6/1993 | Gouge et al. . |
| 5,255,683 | 10/1993 | Monaghan . |
| 5,285,788 | 2/1994 | Arenson et al. . |
| 5,610,134 | 3/1997 | Clark et al. . |
| 5,664,571 | 9/1997 | Yamazaki ................................. 600/441 |
| 5,710,172 | 1/1998 | Kukreja et al. . |
| 5,724,976 | 3/1998 | Mine et al. ............................... 600/459 |
| 5,735,281 | 4/1998 | Rafter et al. ............................. 600/458 |
| 5,882,306 | 3/1999 | Ramamurthy et al. .................. 600/441 |

OTHER PUBLICATIONS

Armstrong, WF et al. "Assessment of Myocardial Perfusion Abnormalities with Contrast–Enhanced Two–Dimensional Echocardiography" *Circulation* (1982) vol. 66, pp. 166–173 published in US.

Aronson, S. "Intraoperative Assessment of Myocardial Perfusion and Cardioplegia Distribution with Contract Echocardiography in Patients with Myocardial Ischemia" (no date) from University of Chicago, Department of Anesthesia & Critical Care, 4 pages, presented in US.

Porter, TR et al. "Noninvasive identification of acute myocardial ischemia and reperfusion with contrast ultrasound using intravenous perfluoropropane–exposed sonicated dextrose albumin" *J. Am Coll. Cardiol.* (Jul. 1995) vol. 26, pp. 33–40, published in US.

Sabia, PJ et al. "Functional Significance of Collateral Blood Flow in Patients With Recent Acute Myocardial Infarction" *Circulation* (1992) vol. 85, No. 6, pp. 2080–2089, originally published in US.

Cheirif, J. et al. "Dobutamine Echocardiography and Myocardial Contrast Echocardiography: Two New Techniques for the Assessment of Myocardial Viability" (1995) *Texas Heart Institute Journal*, vol. 22, No. 1, pp. 33–39, published in US.

Cheirif, J. "Diagnosis of Myocardial Stunning: A New Use for Myocardial Contract and Dobutamine Echocardiography" (Oct. 1995). *American Journal of Cardiac Imaging*, vol. 9, No. 4, pp. 261–268, published in US.

Kaul, S. "An Association Between Collateral Blood Flow and [sic] Myocardial Viability in Patients with Recent Myocardial Infarction", originally printed in *New England Journal of Medicine* (vol. 327, pp. 1825–1831, 1992), reprinted here from *Beyond Angiography* (Nov. 6, 1993), pp. 107–113, originally published in US.

(List continued on next page.)

*Primary Examiner*—Francis J. Jaworski
*Attorney, Agent, or Firm*—Craig A. Summerfield, Esq.; Brinks Hofer Gilson & Lione

[57] ABSTRACT

A method of imaging to aid tissue viability determinations is provided. Tissue motion is detected for at least region of tissue. Perfusion is estimated as a function of intensity data and time for the region of tissue. An image responsive to the detected tissue motion and the estimated perfusion is displayed. A combination of tissue motion imaging and perfusion estimation provides an assessment of tissue viability. If tissue exhibits perfusion and motion, then the tissue is likely normal. Any other perfusion and motion characteristic combination indicates abnormal tissue viability.

42 Claims, 5 Drawing Sheets

OTHER PUBLICATIONS

Kaul, S. "Coronary and Myocardial Blood Volumes. Noninvasive Tools to Assess the Coronary Microcirculation?" (Aug. 5, 1997) *Circulation*, vol. 96, No. 3, pp. 719–724, published in US.

Kaul, S. "Myocardial Contrast Echocardiography. 15 years of Research and Development." (Nov. 18, 1997) *Circulation*, vol. 96, No. 10, pp. 3745–3760, published in US.

Lindner, J.R. and S. Kaul. "Insights into the assessment of myocardial perfusion offered by different cardiac imaging modalities" (Sep./Oct. 1995) *Journal of Nuclear Cardiology*, vol. 2, No. 5, pp. 446–460, published in US.

Pandian, N. "Detection and Quantification of Infarct Size" (Jun. 1996) *Perfusion Imaging Today*, 2 pages, published in US.

Porter, T. "Problems and Challenges in Myocardial Perfusion Imaging" (Jun. 1996) *Perfusion Imaging Today*, 2 pages, published in US.

Powers, J et al. "Innovative Imaging Modalities: Harmonic Imaging, Power Doppler Imaging, and Triggered Mode Imaging: Concepts and Instrumentation" (1996) from Advanced Technology Laboratories, Inc., 4 pages.

Sklenar, J. et al. "Contractile Versus Microvascular Reserve for the Determination of the Extent of Mycardial Salvage After Reperfusion. The Effect of Residual Coronary Stenosis" (Sep. 15, 1996), *Circulation*, vol. 94, No. 6, pp. 1430–1440, published in US.

Villanueva, F. et al. "Coronary Reserve Abnormalities in the Infarcted Myocardium. Assessment of Myocardiabl Viability Immediately Versus Late After Reflow by Contract Echocardiography" (Aug. 15, 1996) *Circulation*, vol. 94, No. 4, pp. 748–754, published in US.

Walker, K.W. et al. "Second Harmonic Mode imaging Enhances Detection of Low Concentrations of Aerosomes® MRX115 Echocontrast Agent In Vitro" (presented Nov. 13–16, 1995) Abstracts of American Heart Association 68th Scientific Sessions, 1 page, published in US.

DeMaria, AN et al. "Echocardiographic Visualization of Myocardial Perfusion by Left Heart and Intracoronary Injections of Echo Contrast Agents" *Circulation*, Abstracts of the 53rd Scientific Sessions, (1980) vol. 62, supplement, III, p. 143, published in US [abstract only].

Ito, H et al. "Lack of Myocardial Perfusion immediately after Successful Thrombolysis: A predictor of poor recovery of left ventricular function in anterior myocardial infarction" *Circulation* (May 1992), vol. 85, No. 5, pp. 1699–1705, published in US.

Sabia, PJ et al. "An association between collateral blood flow and myocardial viability in patients with recent myocardial infarction" *The New England Journal of Medicine* (Dec. 24, 1992), vol. 327, No. 26, pp. 1825–1831, published in US.

Schrope, BA and VL Newhouse "Second Harmonic Ultrasonic Blood Perfusion Measurement" *Ultrasound in Med. & Biol.* (1993) vol. 19, No. 7, pp. 376–379.

Xu, J et al. "Contrast Echocardiographic Assessment of Myocardial Perfusion Following Acute Coronary Artery Occlusion and Reperfusion Using Intravenous Injection of Aerosome MRX 115 in Monkeys" *J. Am Coll. Cardiol. Abstracts* (Feb. 1995) p. 204A, published in US [abstract only].

FIG. 2A

BROKEN LINES INDICATE
DUMMY OPERATIONS

FIG. 2B

INTERLEAVED HI POWERED B-MODE AND DTI

REGION OF INTEREST INFORMATION
AND START OF INJECTION INFORMATION

FIG. 5B

ULTRASONIC SYSTEM AND METHOD FOR TISSUE VIABILITY IMAGING

BACKGROUND OF THE INVENTION

This invention relates to an ultrasound system and method for imaging, and in particular, for assisting in medical diagnosis.

Ultrasound imaging may be used to assess the health of tissue within the body. Methods that may be used for this assessment include Doppler based methods, such as Doppler Tissue Imaging. In this method, Doppler based processing is used to measure the velocity of tissue within a region being examined. Knowledge of tissue movement, especially in relation to the motion of the neighboring regions, can indicate tissue health. This method can be used to examine the health of an organ, such as the heart.

Perfusion measurements also provide diagnostic information. Perfusion is the blood flow per unit of tissue mass that supplies the tissue with oxygen and nutrients (volume/(time*mass)). Ultrasound systems may also be used to estimate perfusion. Methods that attempt to estimate perfusion include measuring the wash in and wash out times of contrast agents injected into the blood stream at a region of interest as the contrast agent enters and exits the region of interest.

Neither the tissue motion nor perfusion methodologies discussed above provide a complete assessment of tissue viability. Viability of tissue is the ability of the tissue to recover and function normally. Therefore, it is desirable to provide an ultrasound method and apparatus for tissue viability imaging.

SUMMARY

The present invention is defined by the following claims, and nothing in this section should be taken as a limitation on those claims. By way of introduction, the preferred embodiment described below includes a method and system for tissue viability imaging. A combination of tissue motion imaging and perfusion estimation provides an assessment of tissue viability. If tissue exhibits perfusion and motion, then the tissue is likely normal. Any other perfusion and motion characteristic combination indicates other conditions, including abnormal tissue viability.

In one embodiment, a method of imaging to aid tissue viability determinations is provided. Tissue motion is detected for at least one region of tissue. Perfusion is estimated as a function of intensity data and time for the at least one region of tissue. An image responsive to the detected tissue motion and the estimated perfusion is displayed.

In another embodiment, a method of imaging to aid tissue viability determinations is provided. Tissue motion is detected for at least one region of tissue. Perfusion is estimated as a function of intensity data for the at least one region of tissue. A color corresponding to tissue viability is determined as a function of the tissue motion and the perfusion for the at least one region. An image responsive to the color is displayed.

Further aspects and advantages of the invention are discussed below in conjunction with the preferred embodiments.

DETAILED DESCRIPTION OF PREFERRED EMBODIMENTS

An ultrasound image based on tissue motion and tissue perfusion information may provide an indication of tissue viability. If perfusion is detected and no tissue motion is observed, the tissue region may be hibernating and may be salvageable via surgical intervention. If no perfusion and no motion are detected, the tissue region may be necrotic. If no perfusion is detected and the motion of the region is normal, the perfusion estimator likely did not correctly estimate perfusion.

Figure 1:
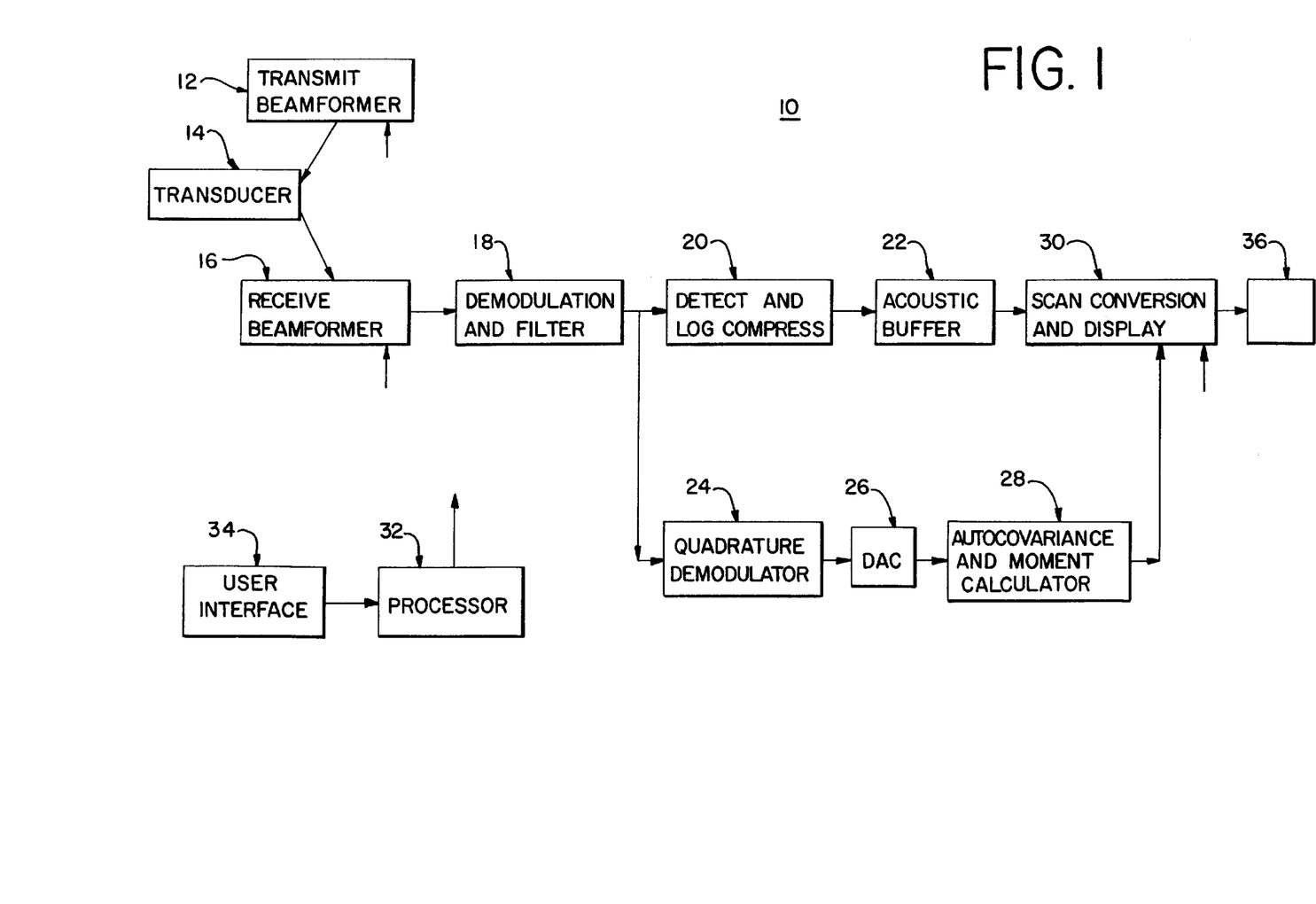
FIG. 1 is a block diagram of one embodiment of an ultrasound system of the present invention for tissue viability imaging.

Referring to FIG. 1, a preferred embodiment of an ultrasound system for generating a tissue viability image is shown generally at 10. The system 10 includes a transmit beamformer 12, a transducer 14, a receive beamformer 16, and a demodulator and filter 18 as a beamformer path. A B-mode processing path is connected in parallel with a Doppler processing path to the beamformer path. The B-mode processing path includes a detector and log compressor 20 and an acoustic buffer 22, and the Doppler processing path includes a quadrature demodulator 24, digital to analog converter 26 and an autocovariance and moment calculator 28. The B-mode processing path provides intensity information for perfusion estimation, and the Doppler processing path provides velocity, variance or energy information as tissue motion information. A scan converter 30 also connects to the B-mode and Doppler processing paths. A display 36 connects to the scan converter 36. Other processing paths including different, additional or fewer components may be used.

During operation, the transmit beamformer 12 provides excitation signals to the transducer 14, such that ultrasound beams are focused within a region. The ultrasonic energy is reflected from impedance mismatches within the body. Some of the reflected energy impinges on the transducer 14. Signals associated with the reflected energy are amplified and provided to the receive beamformer 16. The receive beamformer 16 sums the signals from the various elements of the transducer 14 after applying appropriate delays. The summation is performed such that a continuous focus is maintained. The summed signals are demodulated and filtered by the demodulation and filter block 18. The demodulated and filtered signals are provided to the B-mode and Doppler processing paths.

For B-mode processing, the signals are detected and log compressed in the detector and log compressor 20. The resulting information is stored in the acoustic buffer 22. After an entire scan of a region or a frame of data is acquired, the data is output from the acoustic buffer 22 to the scan converter 30. Other processing paths and associated techniques for generating ultrasound intensity or B-mode information may be used.

For tissue motion processing, the demodulated and filtered signal is provided to the quadrature demodulator 54. The quadrature demodulator 54 demodulates and low pass filters the information. The digital to analog converter 26 converts the analog information to digital samples. The digital samples are filtered to obtain information associated with desired motion (i.e. tissue motion). For example, a user is able to select from different filters, each with different values of low velocity cut-off. Signals from non-moving tissue and slowly moving blood are removed from the information. The autocovariance and moment calculator 28 determines the autocovariance coefficients $R(0)$, $R_0(0)$, $R_1(0)$ of the filtered samples. From these coefficients, the mean velocity, variance and energy of the Doppler information is found. Other tissue motion processing paths may be used, such as fully digital, fully analog or cross-correlation (i.e. one or two-dimensional displacement as a function of multiple target interrogations) processing paths. Furthermore, velocity may be estimated as disclosed in U.S. Pat. No. 5,285,788.

The tissue motion and intensity information is provided to the scan converter 30. The scan converter 30 combines the intensity information and tissue motion information to generate a tissue viability image as discussed below. Preferably, the scan converter 30 preserves the spatial orientation of the information.

A processor 32 controls the timing and transfer of data between and through the various processing paths discussed above. The control of the system is responsive to information from a user interface 34. Preferably, the user configures the system 10 for tissue viability imaging. The system 10 is capable of estimating perfusion, and estimation of tissue motion, B-mode or tissue viability images. For tissue viability imaging, the initial configuration may comprise the generation of a B-mode image, but a different mode of imaging or combination of modes of imaging may be used. Based on the image or other information, the user selects a region or regions for measurement or tissue viability imaging. In alternative embodiments, the region or regions are selected using software algorithms or other processes. In the preferred embodiment, the user also selects an appropriate perfusion estimation technique, such as wash-in, wash-out, triggering, binary indication or combinations thereof. Other perfusion techniques and configuration selections may be used.

Various embodiments may aid in tissue viability imaging. For example, using fundamental imaging, velocity of tissue, such as the myocardium, may be measured and using harmonic imaging, perfusion estimates may be obtained, provided that contrast agents with a good harmonic response were injected into the blood stream.

In one embodiment, the user may configure the system 10 for harmonic or fundamental frequency imaging, such as obtaining the B-mode information from harmonic echo information and the Doppler tissue motion information from fundamental echo information. Any of the data associated with the various modes discussed herein may be associated with harmonic or fundamental based echo information.

After configuring the system 10 and injecting any contrast agent, the system 10 transmits multiple ultrasound waves for a plurality of lines for tissue viability imaging. Preferably, the effects of artifacts, such as rib shadow and lung artifacts, are minimized or accounted for by having the patient hold their breath, using a small transducer, selecting an appropriate image window or using a negative offset imaging format such as taught by U.S. Pat. No. 4,550,607.

Various transmission and receive techniques may be used, such as receiving multiple lines in a single operation based on one transmission. Preferably, ultrasonic transmissions associated with B-mode imaging are interleaved with ultrasonic transmissions associated with tissue motion imaging, such as line or frame interleaving.

Figure 2A:
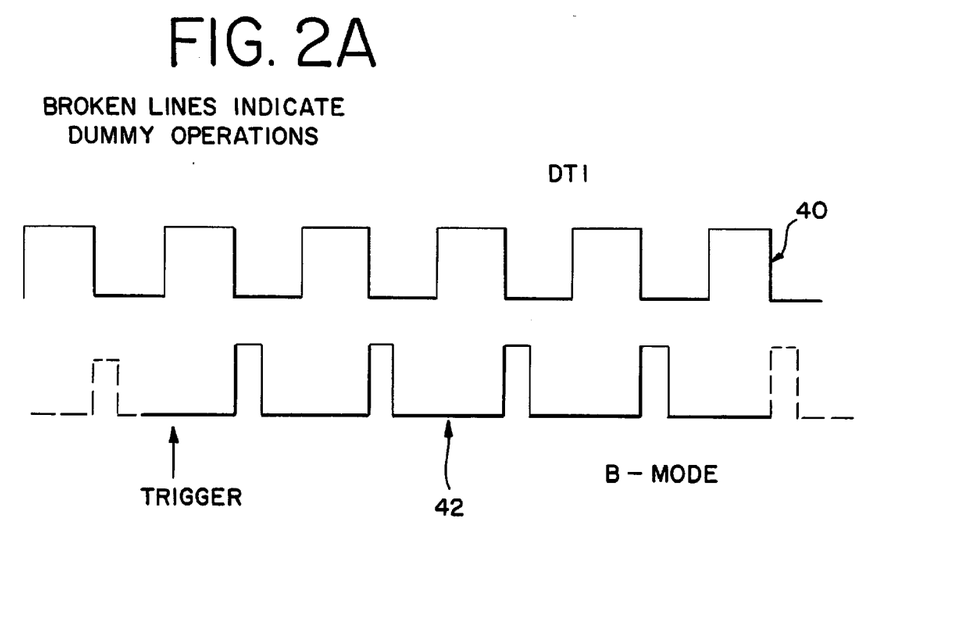
FIG. 2A is a graphic representation of one embodiment of interleaving ultrasonic transmissions associated with tissue motion and B-mode imaging.

Referring to FIG. 2A, a timing diagram of one embodiment for interleaving Doppler tissue motion information and B-mode information is shown. A trace 40 demonstrates a transmission and reception process for obtaining tissue motion information (e.g. Doppler velocity estimates) along one scanning line. A trace 42 represents the transmit and receive processing for B-mode information. Since multiple transmit and receive operations are not required for B-mode processing, the time required to obtain the B-mode information is less than the time required for the tissue motion information of trace 40. For example, the solid portion of trace 42 represents the interleaving of B-mode transmissions and receptions and is less than the time used for obtaining the Doppler information represented by trace 40. By successively interleaving B-mode and Doppler operations, the entire user selected region of interest is interrogated by scanning along multiple lines. By line inter-leaving, any high power transmissions for one imaging mode may not destroy contrast agent prior to transmissions for another imaging mode. Other timing and interleaving of transmission events may be used.

Any of the various methods of transmission as discussed above may be performed at different power levels. For example, transmissions associated with tissue motion imaging may be low power transmissions. The power is selected so that the ultrasonic waves do not destroy any contrast agent. Ultrasonic waves associated with B-mode harmonic imaging are also preferably associated with low power, so as not to destroy any contrast agent. In alternative embodiments, either one or both of Doppler tissue motion or B-mode perfusion imaging are associated with higher power transmission (e.g. contrast agent destructive power levels).

Figure 2B:
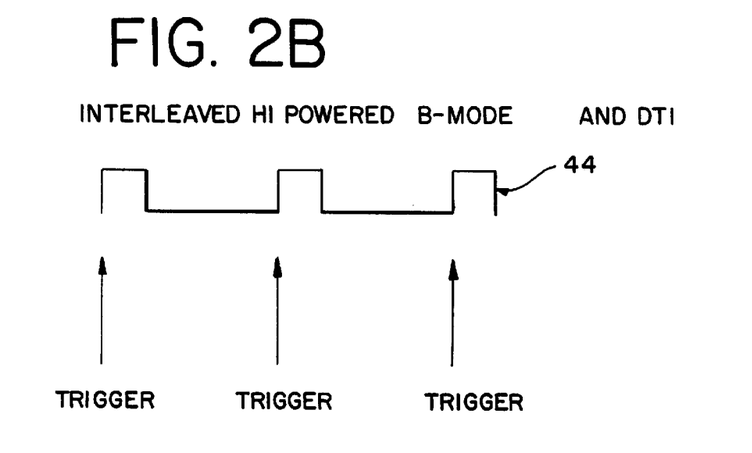
FIG. 2B is a graphic representation of one embodiment of triggering ultrasonic transmissions.

Preferably, higher power transmissions are associated with triggering. Referring to FIG. 2B, a timing diagram demonstrating the interleaved transmission for Doppler tissue motion imaging and perfusion estimations using triggering is shown (trace 44). For triggering, the system 10 (FIG. 1) initiates a scanning sequence for transmission and reception once a trigger is detected. Preferably, an EKG module provides a heart cycle signal to the system 10. Based on the heart cycle signal and control software, the system 10 initiates transmission and reception.

Various triggers, including an R-wave or other portions of the heart cycle or other detected events, may be used. For heart cycle triggering of tissue motion imaging, the triggers are preferably set between peak systolic or diastolic portions of the heart cycle. At peak systole or diastole, the motion of the heart is minimal. Alternatively, multiple triggers within a single heart cycle or a trigger that varies within the heart cycle over a plurality of heart cycles are used. In alternative embodiments, multiple triggers may occur before a scanning sequence is initiated, such as scanning every second or third R wave. Furthermore, the scanning sequence may consist of acquiring one or more frames of B-mode data, Doppler data, or combinations thereof after each trigger.

Preferably, interleaved frames of one each of harmonic B-mode and a fundamental Doppler information associated with high power transmissions are obtained after each trigger. The system 10 may acquire additional data after each subsequent trigger.

Other combinations of power level and imaging mode may be used with various triggers. For example, acquisition of B-mode data associated with high powered transmission may be triggered, and acquisition of Doppler data associated with lower power transmissions may be continuous. Preferably, the tissue viability imaging is finished over a period of three or four heart cycles. If a larger interval of time is used, new areas of the heart may enter the user specified region of interest and may adversely affect perfusion estimation. Preferably, the patient is held steady or holds their breath to avoid unnecessary movement. The system 10 may also operate without triggering regardless of transmission power levels.

Based on the transmission and reception of information for tissue motion imaging, motion or velocity values are estimated as discussed above. Perfusion estimates are calculated from B-mode or intensity information instantaneously or as a function of time.

Various techniques may be used for estimating perfusion, including time intensity, triggering, absolute perfusion and binary indication. Other techniques for estimating perfusion may be used.

For the binary indication technique, contrast agents are preferably injected into the patient's blood stream. The contrast agent travels to the region of interest, such as the myocardium. A greater amount of contrast agent is present in areas where perfusion is not hindered or is high, than in areas with low perfusion or blood flow. Areas with greater amounts of contrast agent are associated with higher intensities. The intensity information may be averaged as a function of time for accuracy or instantaneous values may be used. High intensity B-mode information in a region indicates high perfusion, and low intensity B-mode information indicates low perfusion. Based on the intensity level and one or more thresholds, perfusion is estimated to exist, exist at different levels or not exist.

Perfusion may also be estimated with time intensity methods, such as wash-in, wash-out or wash-in wash-out techniques. For example, contrast agents are injected. A region of interest is imaged over a time period. The change of intensity at the region of interest over the time period is measured. Various functions, such as a summation or average of intensities for a region of interest, may be used, and any region of interest may be subdivided into one or more regions of interest for separate perfusion estimation. Preferably, the system 10 accounts for any non-linear processing (i.e., a change in intensity is not equal to a change in the amount of contrast agent). The intensity level increases as the contrast agent enters the region of interest, and the intensity decreases as the contrast agent leaves the organ. Based on the intensity level or B-mode information, the transit time of the contrast agent through the organ is calculated and is inversely related to blood flow.

Figure 4A:
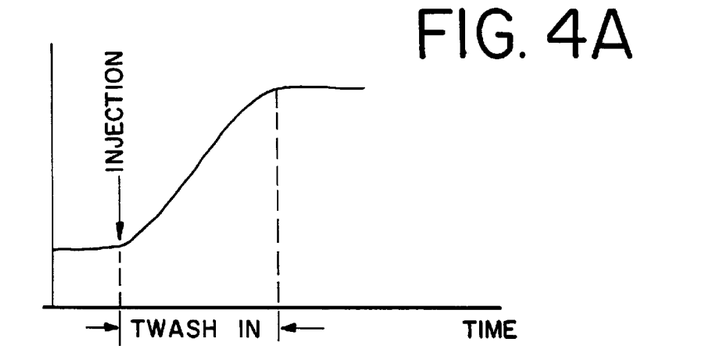
FIGS. 4A through 4C are graphic representations of wash-in and wash-out curves.
Figure 4B:
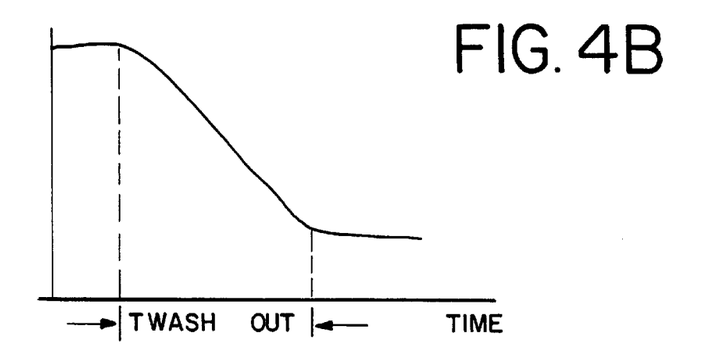
Figure 4C:
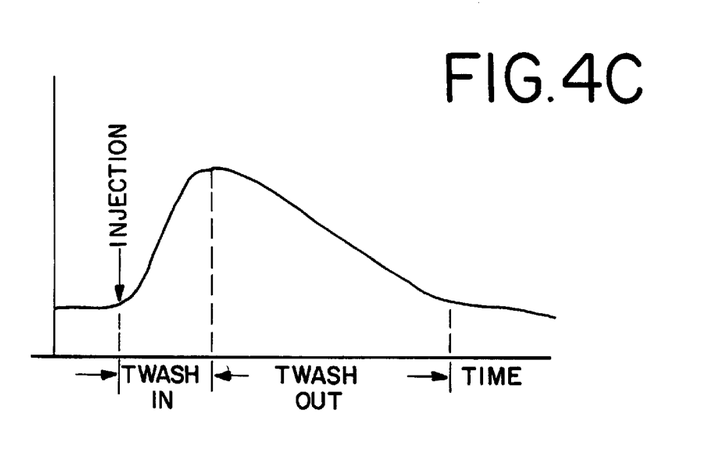

The type of time intensity estimation is a function of the time period selected. Referring to FIG. 4A, an example of a wash-in curve is represented. The curve represents an average or summed intensity as a function of the time from injection to the time to reach a peak intensity value. Referring to FIG. 4B, an intensity curve representing a wash-out curve is shown. Perfusion is estimated from the amount of time for the contrast agent to transit from a peak intensity value to a minimum value. Referring to FIG. 4C, a wash-in wash-out intensity curve is represented. Both wash-in and wash-out transit times of contrast agents are measured as discussed above. For the time intensity perfusion estimations discussed above, various time periods as a function of intensity may be measured, such as times from or to intensities at a percentage above or below the peak and minimum intensity values. Preferably, any percentages are determined through experimentation, and may be about 10 to 20 percent of the peak and minimum intensity values. Furthermore, either continuous or triggered imaging may be used for time intensity calculations.

Perfusion may be estimated using triggering. For example, a triggering rate is varied. Preferably, high power ultrasonic waves are transmitted at each trigger and the intensity of the echoes is measured. Based on the resulting destruction of the contrast agent, the triggering rate is adjusted to maintain a steady state intensity. If the triggering rate or time between triggers is low, intensity increases. If the triggering rate is too rapid, the intensity decreases due to contrast agent destruction. The rate of triggering (i.e. the time period between triggered frames) associated with a steady state intensity estimates perfusion.

Perfusion may be estimated using absolute perfusion calculations, such as described in U.S. application Ser. No. 08/949,237 for AN ULTRASONIC METHOD AND SYSTEM FOR MEASURING PERFUSION, filed Oct. 10, 1997, the disclosure of which is herein incorporated by reference. For absolute perfusion, contrast agent is constantly infused with an infusion pump. Preferably, the Doppler imaging is associated with lower power transmission. After a constant intensity at the region of interest is established, a high powered ultrasonic wave is transmitted to destroy the contrast agent. Either triggers or the user activate transmission of the high power ultrasonic wave. The increase in intensity after transmission of the high power ultrasonic wave is used to estimate perfusion. In a preferred embodiment, the absolute measure of perfusion is determined from the equation: $\ln[c(t\alpha)-c(t)]=\ln[c(t\alpha)-c(t0)]-(fV)t$, where $c(t\alpha)$ is the concentration of contrast agent at infinity (i.e. a steady state value), $c(t)$ is the concentration of contrast at time t, f is the true blood flow rate and V is the volume fraction of blood within the region of interest. Preferably, the concentration is a measure of the intensity at a point in the processing paths where signals are linear. The fraction f/V is the absolute measure of flow per unit volume. Other equations may be used.

Referring to FIG. 1, the tissue motion information is provided to the scan converter 30. Perfusion is estimated in the B-mode processing path or the scan converter 30. Alternatively, the tissue motion information is provided to a processor for tissue viability determination prior to the scan converter 30, and the processor estimates perfusion. Referring to FIG. 3B, the tissue motion information and perfusion estimates are combined in a lookup table 50 in the scan converter 30. In alternative embodiments, processors, hardware or software combine the tissue motion information with the perfusion estimates.

In the preferred embodiment, the tissue motion data and the perfusion estimates address a two-dimensional memory map. Based on the address selections, a color display value (e.g., RGB or YUV) is output by the lookup table 50.

Figure 3A:
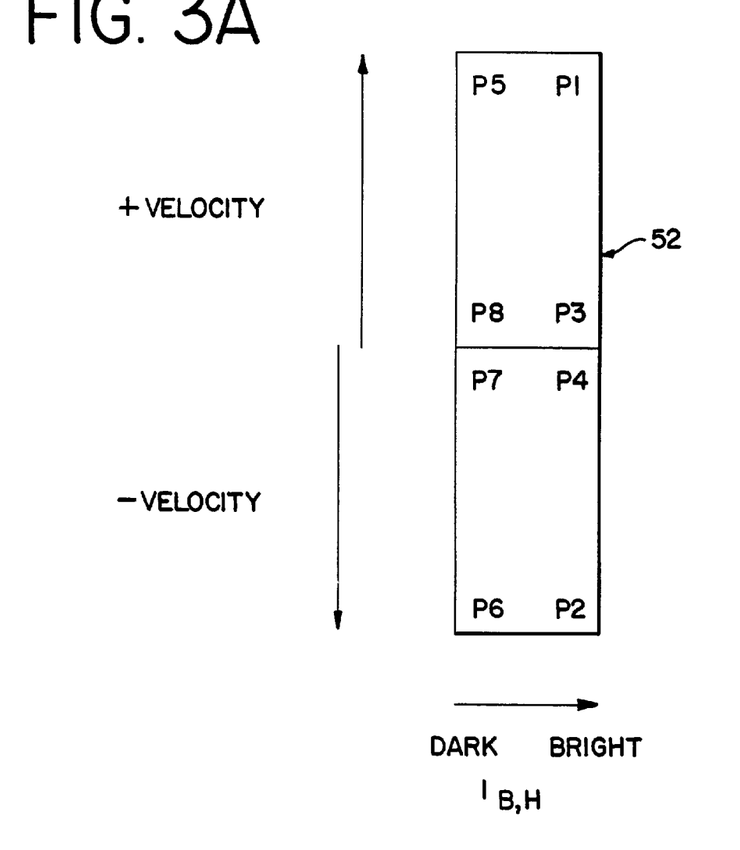
FIG. 3A is a graphic representation of one embodiment of a display key for the present invention.
Figure 3B:
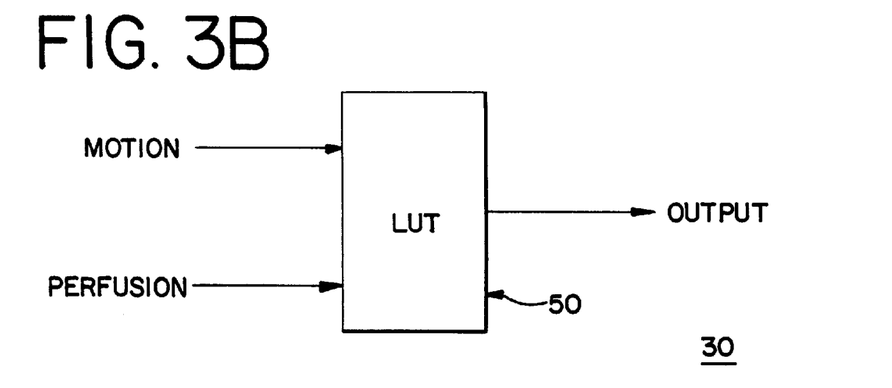
FIG. 3B is a block diagram of a preferred embodiment of a lookup table for implementing the key of FIG. 3A.

Referring to FIG. 3A, a preferred two-dimensional memory map is graphically demonstrated. Tissue motion is estimated from Doppler velocity values, and perfusion is estimated from B-mode intensity information collected instantaneously or over time. For example, perfusion is estimated using the absolute or binary techniques discussed above. The velocity information is plotted on the y-axis with positive velocities increasing in the positive y direction and negative velocities increasing in the y-direction. Positive velocities are encoded by red blending towards yellow as the velocity increases and negative velocities are encoded in blue blending towards green as the negative velocities increase. In alternative embodiments, different colors are used or the same colors may be used for both positive and negative velocities. Intensities or perfusion estimate information is encoded along the x-axis, either by a separate color or a brightness of the colors associated with velocity. Other encoding techniques may be used. Preferably, the brightness of the color increases along the x-axis. In a preferred embodiment, strong signals from the contrast agent or high perfusion estimates are encoded by colors to the right of a primary memory map, such as represented by map 52 and weak signals or estimates are encoded by colors to the left of the map 52.

Figure 5A:
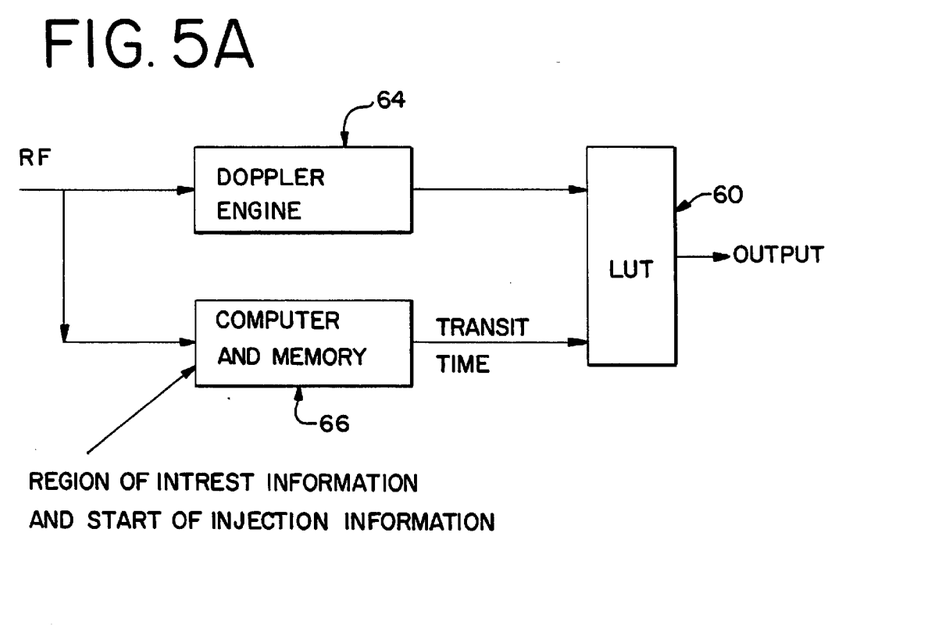
FIG. 5A is a graphic representation of another embodiment of a display key.
Figure 5B:
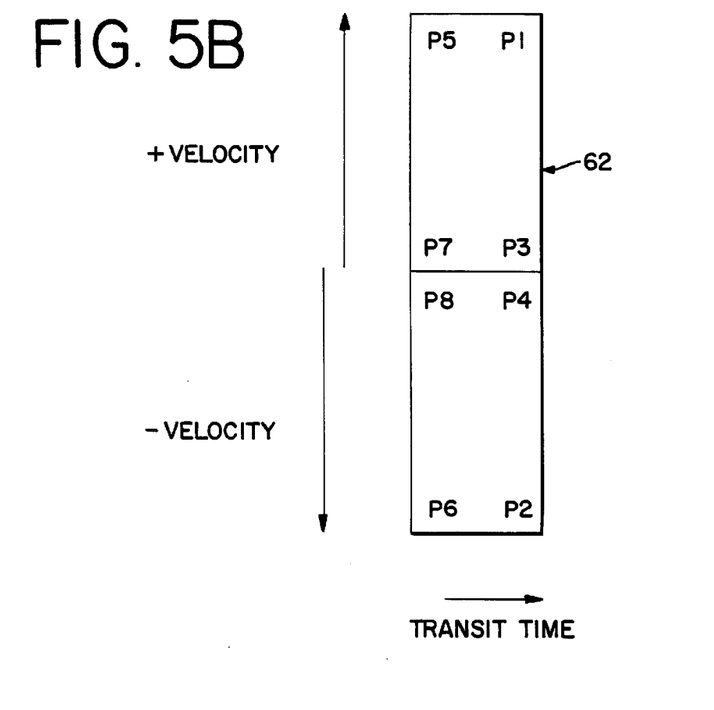
FIG. 5B is a block diagram of one embodiment of a lookup table structure for implementing the display key of 5A.

Referring to FIGS. 5A and 5B, a preferred embodiment of a lookup table 60 and corresponding memory map, such as represented by map 62 for use with time intensity estimation of perfusion is shown. In this embodiment, tissue motion is estimated from Doppler velocity or energy by a Doppler engine 64. The Doppler engine 64 preferably operates in the manner described above for the Doppler processing path to provide tissue motion estimates to the lookup table 60. The lookup table 60 also receives transit time information as an estimate of perfusion from the computer and memory 66. The radio frequency (RF) information input into the computer and memory 66 and the Doppler engine 64 is preferably coherently summed and, demodulated and filtered. The computer and memory 66 determines the line number and sample number of the polar coordinate RF information given the Cartesian coordinates of the region of interest selected by the user. Based on the intensity of the RF data, perfusion is estimated as discussed above for the region of interest or multiple regions of interest. Since RF data is input, the absolute value or the magnitude of the echoes is preferably utilized as the intensity. Based on a start of injection signal or an amount of time between selected minimum and maximum intensity values, the computer and memory 66 calculates the transmit time. In alternative embodiments, detected data is used to calculate time intensity curves. For this alternative embodiment, the computer and memory 66 is placed in the data path after the RF data is detected. Preferably, the data is obtained before log compression or is linearized before processing. In alternative embodiments, log compressed or scan converted data is input to the computer and memory 66.

Referring to the map 62, the tissue motion and perfusion estimate information is provided as addresses for each point within a region. Tissue motion, such as Doppler velocity estimates, are plotted along the y-axis of the map 62 as discussed above for map 52 (FIG. 3B). The transit time is encoded along the x-axis of the map 62 in a manner similar to the intensity or perfusion data of map 52 (FIG. 3B). Preferably, the maximum transit time is encoded as small x-axis values and small transit times are encoded as high x values of the map 62. Small transit times indicate high blood flow, and high blood flow indicates good perfusion. Other mapping patterns may be used.

Referring to FIGS. 3 and 5, the output signals are used to generate an image indicating tissue viability. For the preferred map patterns discussed above, regions encoded by colors at p1 and p2 of FIGS. 3A and 5B indicate good perfusion and tissue motion (i.e., healthy, normal tissue). Regions encoded by a color associated with p3 or p4 indicate that perfusion was detected but no tissue motion was observed, such as associated with hibernating tissue. Regions encoded with colors associated with p5 and p6 indicate tissue motion associated with little or no perfusion, such as erroneous imaging. Regions encoded by colors associated with p7 and p8 may indicate no motion or perfusion, such as associated with necrosis of tissue. More or fewer colors than the eight (p1–p8) discussed above may be used. For example, only one dark or bright selection for perfusion and a range of three or more tissue motion colors are used for binary indication. Three or more levels of brightness or color changes as a function of perfusion may be used for any of the various perfusion techniques.

Referring to FIG. 1, the output signals are used to generate an image on the display 36. Preferably, a two-dimensional image is generated where perfusion is estimated for multiple spatial locations or pixels on the display. The perfusion estimate calculated for a region is used for each spatial location within that region. The tissue viability image may be combined with other images, such as overlaying a B-mode image. In alternative embodiments, the tissue viability image is generated by displaying an image responsive to the tissue motion estimates adjacent an image responsive to perfusion estimates. A perfusion estimation image may be overlaid on the tissue motion estimate image.

In a preferred embodiment, a color key is displayed adjacent to the tissue viability image. For example, one of the maps 52 and 62 of FIGS. 3A and 5A, respectively, is represented by the color key or legend display. The color key is preferably displayed adjacent to the tissue viability image.

As discussed above, various modes of processing may be used to estimate tissue motion or perfusion. In one alternate embodiment, tissue motion is estimated with data generated in a strip Doppler mode. Strip Doppler data is associated with a point or region within a patient and the display of a frequency spectrum along a y-axis and time along the x-axis. The strip display is preferably a gray scale display. The strength at a particular frequency modulates the brightness. For tissue viability imaging, the estimated perfusion associated with the region is represented by adding color to the strip display. In alternate embodiments, the perfusion estimation is associated with brightness and the energy or strength at a particular frequency is associated with color.

Based on the combination of tissue motion and perfusion estimation through adjacent, overlay or mapped information, the user assesses tissue viability. While the invention has been described above by reference to various embodiments it will be understood that many changes and modifications can be made without departing from the scope of the invention. For example, different memory maps and different types of information along the x- or y-axis may be used. Different, including novel, perfusion or tissue motion estimating techniques may be used, such as techniques not using contrast agents.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method of imaging to aid tissue viability determinations comprising the steps of:

(a) detecting tissue motion corresponding to at least one point of in a tissue;

(b) estimating perfusion as a function of intensity data and time for the at least one point; and (c) displaying an image responsive to the detected tissue motion and the estimated perfusion.

2. The method of claim 1 wherein step (c) comprises displaying a first image responsive to the detected tissue motion adjacent a second image responsive to the estimated perfusion.

3. The method of claim 1 wherein step (c) comprises overlaying a first image responsive to the estimated perfusion on a second image responsive to the detected tissue motion.

4. The method of claim 1 wherein step (c) comprises:
(c1) inputting first and second signals responsive to the detected tissue motion and the estimated perfusion, respectively;
(c2) outputting a third signal responsive to the first and second signals;
(c3) displaying the image responsive to the third signal.

5. An apparatus for imaging to aid tissue viability determinations, the apparatus comprising:
a processing structure for detecting tissue motion corresponding to at least one point of the tissue and for estimating perfusion as a function of intensity data and time for substantially the at least one point; and
a display device for displaying an image responsive to the detected tissue motion and the estimated perfusion.

6. The apparatus of claim 5 wherein the processing structure comprises at least two processors, one of said two processors for detecting tissue motion and another of said two processors for estimating perfusion.

7. The apparatus of claim 5 wherein the display device comprises a display device for displaying a first image responsive to the detected tissue motion adjacent a second image responsive to the estimated perfusion.

8. The apparatus of claim 5 wherein the display device comprises a display device for overlaying a first image responsive to the estimated perfusion on a second image responsive to the detected tissue motion.

9. The apparatus of claim 5:
further comprising a mapping table structure for receiving first and second signals responsive to the detected tissue motion and the estimated perfusion, respectively, and for outputting a third signal responsive to the first and second signals; and
wherein the display device comprises a display for displaying the image responsive to the third signal.

10. A method of imaging to aid tissue viability determinations comprising the steps of:
(a) detecting tissue motion corresponding to at least one point of a tissue;
(b) estimating perfusion as a function of intensity and time for the at least one point; and
(c) outputting a signal responsive to the detected tissue motion and the estimated perfusion;
(d) displaying an image responsive to the signal.

11. The method of claim 10 wherein step (a) comprises Doppler processing.

12. The method of claim 11 wherein step (d) comprises displaying a color coded Doppler strip of frequency as a function of time.

13. The method of claim 10 wherein step (a) comprises correlation processing.

14. The method of claim 10 wherein step (b) comprises providing contrast agents.

15. The method of claim 14 wherein step (b) comprises calculating a transit time as a function of intensity.

16. The method of claim 14 wherein step (b) comprises:
(b1) substantially destroying contrast agents at the at least one point; and
(b2) calculating perfusion as a function of intensity and time.

17. The method of claim 14 wherein step (b) comprises:
(b1) triggering ultrasonic transmissions;
(b2) adjusting a triggering rate in response to intensity; and
(b3) calculating perfusion as a function of the triggering rate.

18. The method of claim 14 wherein step (b) comprises calculating a B-mode intensity value.

19. The method of claim 18 wherein step (b) comprises calculating a linear B-mode intensity value.

20. The method of claim 10 wherein step (b) comprises obtaining harmonic B-mode intensity data.

21. The method of claim 10 wherein step (c) comprises outputting the signal from a mapping structure.

22. The method of claim 21 wherein step (c) comprises outputting a color value from a two-dimensional look-up table.

23. The method of claim 10 wherein the at least one point comprises a region and wherein step (d) comprises displaying the image as a two-dimensional image of at least the region.

24. An apparatus for imaging to aid tissue viability determinations, the apparatus comprising:
a processing structure for detecting tissue motion corresponding to at least one point of a tissue and for estimating perfusion as a function of intensity data and time for substantially the at least one point;
a mapping structure for receiving first and second signals responsive to the detected tissue motion and the estimated perfusion, respectively, and for outputting a third signal responsive to the first and second signals; and
a display device for displaying an image responsive to the third signal.

25. The apparatus of claim 24 wherein the processing structure comprises a processor selected from the group consisting of: Doppler and correlation processors.

26. The apparatus of claim 24 wherein the processing structure is operable to calculate a transit time as a function of intensity.

27. The apparatus of claim 24 further comprising a means for substantially destroying contrast agents at the at least one point; and wherein the processing structure is operable to calculate perfusion as a function of a steady state intensity, a post destruction intensity and time.

28. The apparatus of claim 24:
further comprising a means for triggering ultrasonic transmissions; and
wherein the processing structure is operable to adjust a triggering rate in response to intensity measurements and to calculate perfusion as a function of the triggering rate.

29. The apparatus of claim 24 wherein the intensity data comprises linear B-mode values.

30. The apparatus of claim 24 wherein the intensity data comprises harmonic B-mode data.

31. The apparatus of claim 24 wherein the mapping structure comprises a look-up table.

32. The apparatus of claim 31 wherein the third signal comprises a color value.

33. The apparatus of claim 24 wherein the image comprises a color coded Doppler strip of frequency as a function of time.

34. The apparatus of claim 24 wherein the at least one point comprises a region and wherein the image comprises a two-dimensional image of at least the region.

35. A method of imaging to aid tissue viability determinations comprising the steps of:
   (a) detecting tissue motion corresponding to at least one region of a tissue;
   (b) estimating perfusion as a function of intensity for the at least one region;
   (c) outputting a tissue viability display value representing one of at least three viability states associated with the at least one region and responsive to the detected tissue motion and the estimated perfusion; and
   (d) displaying a tissue viability image responsive to the tissue viability display value.

36. The method of claim 35 wherein step (b) comprises estimating the perfusion as a binary indication.

37. The method of claim 35 wherein step (b) comprises estimating the perfusion as an absolute perfusion calculation.

38. The method of claim 35 wherein step (b) comprises estimating the perfusion as a calculation selected from the group consisting of: wash-in, washout and washin washout.

39. The method of claim 35 wherein step (b) comprises estimating the perfusion as a function of a triggering rate.

40. The method of claim 35 wherein step (c) comprises outputting a color value.

41. The method of claim 40 wherein step (c) comprises outputting the color value corresponding to one of normal tissue, hibernating tissue, erroneous imaging, and necrosis.

42. An apparatus for imaging to aid tissue viability determination, the apparatus comprising:
   a Doppler processing path for detecting tissue motion corresponding to at least one region of a tissue;
   an intensity processing path for estimating perfusion as a function of intensity data corresponding to the at least one region;
   a look-up table for outputting a tissue viability display value representing one of at least three viability associated with the at lest one region and responsive to the detected tissue motion and the estimated perfusion; and
   a display for displaying a tissue viability image responsive to the tissue viability display value.

* * * * *

UNITED STATES PATENT AND TRADEMARK OFFICE
CERTIFICATE OF CORRECTION

PATENT NO. : 6,015,384
DATED : January 18, 2000
INVENTOR(S) : B. S. Ramamurthy et al.

It is certified that error appears in the above-identified patent and that said Letters Patent is hereby corrected as shown below:

In column 2, line 48, delete "36" and substitute --30-- in its place.

In column 6, lines 37 and 38, delete "$\ln[c(t\alpha)-c(t)] = \ln[c(t\alpha)-c(t0)-(f1V)t$, where $c(t\alpha)$" and substitute --$\ln[c(t_\alpha)-c(t)] = \ln[c(t_\alpha)-c(t_0)]-(f/V)t$, where $c(t_\alpha)$-- in its place.

In column 7, line 3, delete "*y*-direction" and substitute --*y* direction-- in its place.

UNITED STATES PATENT AND TRADEMARK OFFICE
CERTIFICATE OF CORRECTION

PATENT NO. : 6,015,384
DATED : January 18, 2000
INVENTOR(S) : B. S. Ramamurthy et al.

It is certified that error appears in the above-identified patent and that said Letters Patent is hereby corrected as shown below:

In claim 42, line 9, after "viability" insert --states--.

In claim 42, line 10, delete "lest" and substitute --least-- in its place.

Signed and Sealed this

Fifteenth Day of May, 2001

*Attest:*

NICHOLAS P. GODICI

*Attesting Officer*   *Acting Director of the United States Patent and Trademark Office*